United States Patent [19]

Zepf

[11] Patent Number: 5,674,187
[45] Date of Patent: Oct. 7, 1997

[54] HYPEREXTENSION ORTHOSIS WITH IMPROVED FASTENER

[75] Inventor: Armin Zepf, Duderstadt, Germany

[73] Assignee: Otto Bock Orthopaedische Industrie Besitz- und Verwaltungs-Kommanditgesellschaft, Duderstadt, Germany

[21] Appl. No.: 619,349

[22] Filed: Mar. 21, 1996

[30] Foreign Application Priority Data

Mar. 24, 1995 [DE] Germany ............. 295 04 983 U

[51] Int. Cl.⁶ ............................................. A61F 5/00
[52] U.S. Cl. ................................... 602/19; 24/585
[58] Field of Search ................ 602/19; 2/44, 45; 24/585, 635

[56] References Cited

U.S. PATENT DOCUMENTS

| | | | |
|---|---|---|---|
| 4,727,630 | 3/1988 | Alan | 24/585 |
| 4,976,257 | 12/1990 | Akin et al. | 602/19 |
| 5,184,352 | 2/1993 | Maufette | 24/585 |
| 5,259,833 | 11/1993 | Barnett | 602/19 |
| 5,267,679 | 12/1993 | Kamaya et al. | 24/585 X |
| 5,342,289 | 8/1994 | Munny | 602/19 |
| 5,363,863 | 11/1994 | Lelli et al. | 602/19 X |
| 5,388,274 | 2/1995 | Glover et al. | 602/19 X |

FOREIGN PATENT DOCUMENTS

| | | |
|---|---|---|
| 2 629 340 | 10/1989 | France. |
| 39 28 628 | 10/1990 | Germany. |
| WO92/06606 | 4/1992 | WIPO. |

Primary Examiner—Linda C. Dvorak
Attorney, Agent, or Firm—Foley & Lardner

[57] ABSTRACT

A hyperextension orthosis includes a fastener casing mounted on a free end of the orthosis side-piece. The fastener casing releasably receives one end of a waist belt. The fastener casing has a spring arm with a catch on one end. When the waist belt is pushed into an insertion slot extending through the fastener casing, the catch automatically engages under a spring action one of several locking cutouts in the waist belt. The catch can be unlocked by manually pressing together two slides mounted to a frame member of the fastener casing for transverse displacement relative to the insertion slot. At an end opposite the catch, the spring arm has a stud, spring, or the like that engages a groove, bore, or the like in the side-piece in a positive fit.

11 Claims, 2 Drawing Sheets

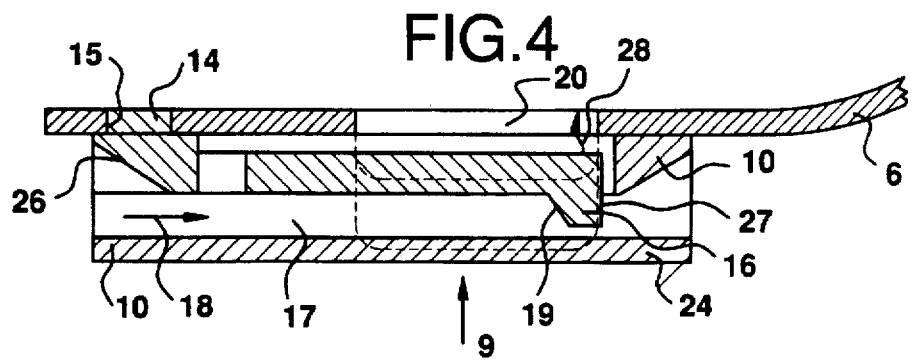
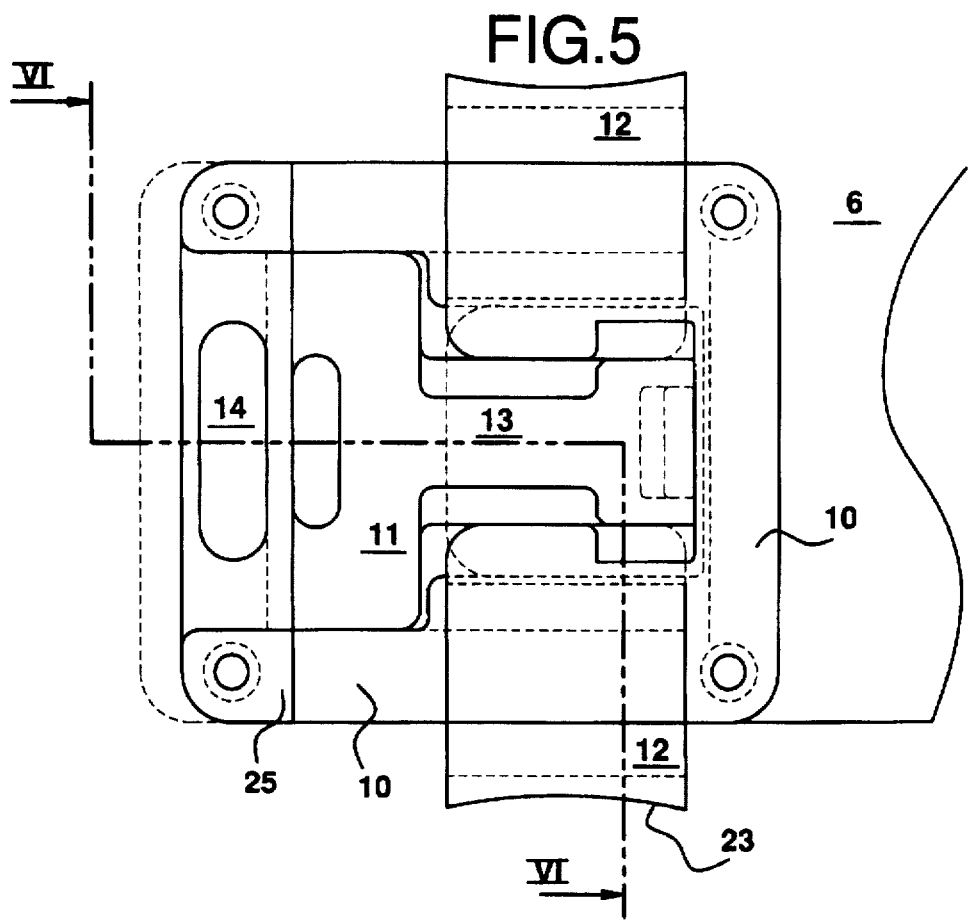
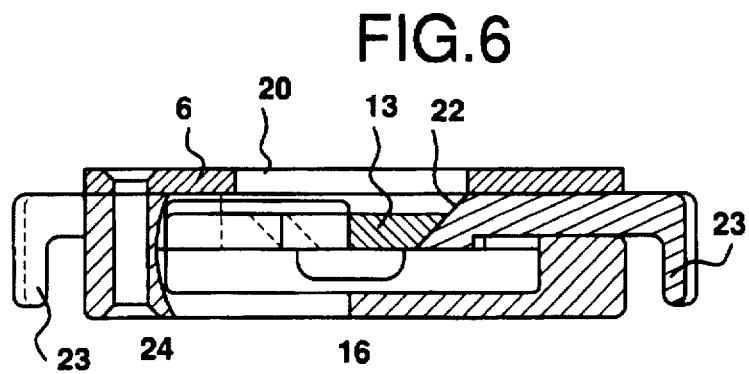

HYPEREXTENSION ORTHOSIS WITH IMPROVED FASTENER

BACKGROUND OF THE INVENTION

This invention relates to a hyperextension orthosis or similar trunk orthoses. More specifically, this invention relates to a fastener apparatus used to releasably secure a hperextension orthosis in place.

A hperextension orthosis—that is, a trunk orthoses which maintains a body trunk in an upright position—generally includes a fastener casing that allows adjustable locking of a waist belt which encircles a wearer's body to hold the orthosis in place. One example of a hyperextension orthosis is disclosed in German Patent No. 39 28 628. The subject invention improves the structure and function of a conventional fastener casing used with hyperextension orthoses.

Accordingly, it is therefore a general object of the invention to provide a hyperextension orthosis which will obviate or minimize difficulties with conventional hyperextension orthoses.

It is a specific object of the invention to provide a hyperextension orthosis which reduces the overall height of the fastener casing.

It is another object of the invention to provide a hyperextension orthosis which absorbs tensile forces applied to a side-piece of the orthosis by structure other than connecting rivets or similar fasteners subject to shearing forces.

It is still another object of the invention to provide a hyperextension orthosis which facilitates unlocking the waist belt from the fastener casing.

SUMMARY OF THE INVENTION

A preferred embodiment of the invention which is intended to accomplish at least some of the foregoing objects include a hyperextension orthosis having a fastener casing attached to a free end of a side-piece of the orthosis. The side-piece extends away from a base plate and receives one end of a waist belt. The waist belt is connected to a back pad. The fastener casing has a catch at one end of a spring arm. The catch protrudes outward, or extends away from, the waist belt. At its end remote from the catch, the spring arm has a stud, spring, or the like, which engages in a positive fit with a bore, groove, or the like in the side-piece. When the waist belt is pushed into an insertion slot extending through the fastener casing, the catch automatically engages one of the locking cutouts in the wist belt under spring action. The catch can be unlocked by manually pressing together two slides which are mounted in the fastener casing for transverse displacement relative to the insertion slot. This manual pressing movement is counter to the spring action. The spring arm, which carries the catch, passes into a recess in the side-piece in its unlocked position.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention.

FIG. 4 is an enlarged side view, in cross section, and shows the spring arm component fitted to the frame component of the fastener casing;

FIG. 5 is a plan view of the spring arm component fitted into the frame component and of opposing slides mounted to the frame component; and FIG. 6 is a side view, in cross section, of the spring arm component fitted into the frame component and of the opposing sides mounted to the frame component, taken substantially along the line A—A in FIG. 5.

DETAILED DESCRIPTION OF THE PREFERRED EMBODIMENTS

Figure 1:
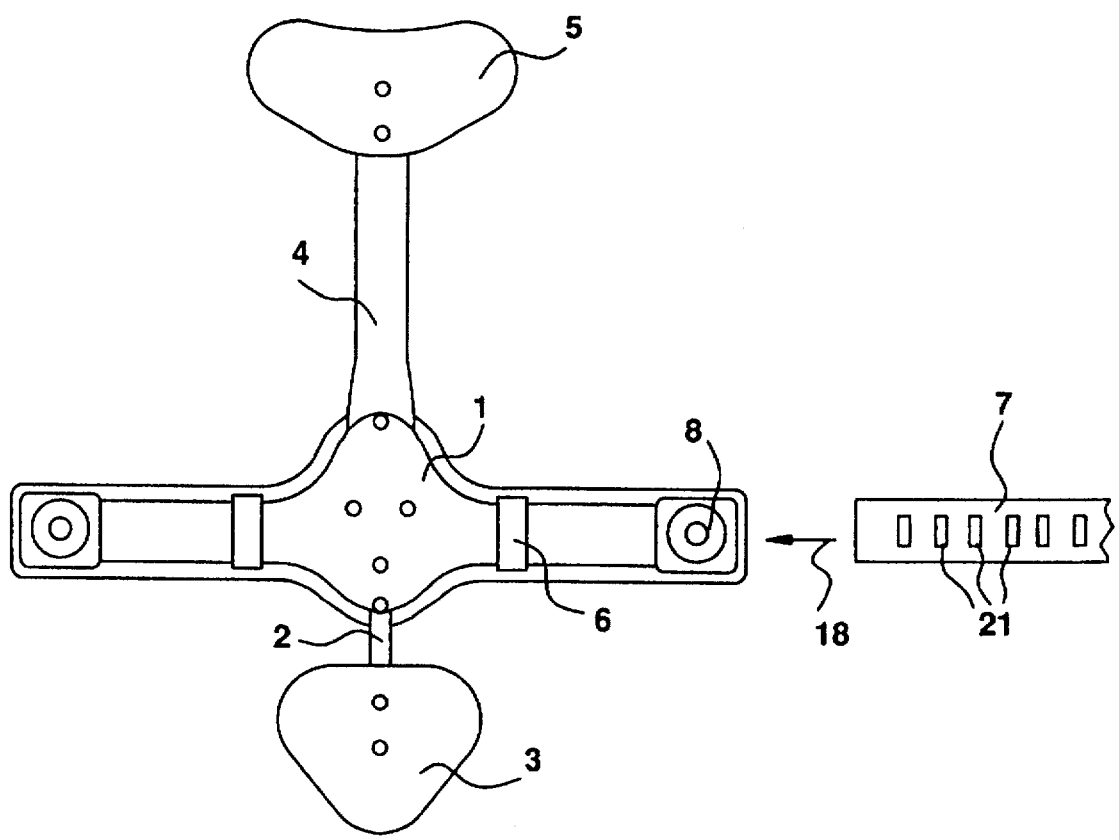
FIG. 1 is a schematic of a front part of a hyperextension orthosis and an end of a waist belt for securing to the hyperextension orthosis in accordance with a preferred embodiment of the invention.

Referring now to the drawings, wherein like numerals indicate like parts, and initially to FIG. 1, there will be seen a front part of a hyperextension orthosis in accordance with the invention. The hyperextension orthosis includes a base plate 1 and an abdominal bar 2 extending downward from the base plate 1. The abdominal bar 2 has a symphysis pad 3 at its lower end. Extending upward from the base plate 1 is a chest bar 4, which has a sternal pad 5 at its upper end. Extending from the base plate 1 on each side are side-pieces 6. The ends of a waist belt 7 are secured at the ends of side pieces 6. The waist belt 7 is connected to a back pad (not shown). A fastener element 8, shown schematically on the rightmost side-piece 6 in FIG. 1, receives an end of the waist belt 7 and secures it to the side piece 6. Although the waist belt is shown only at the rightmost side of the hypertension orthosis, it will be understood by those skilled in the art that the hyperextension orthosis includes a fastener element for receiving an end of the waist belt on the leftmost side-piece as well. The fastener element 8 is the subject of the invention.

The fastener element 8 is a fastener casing, generally indicated 9 in FIG. 4. Side-piece 6 forms the base cover of the fastener casing 9.

Figure 3:
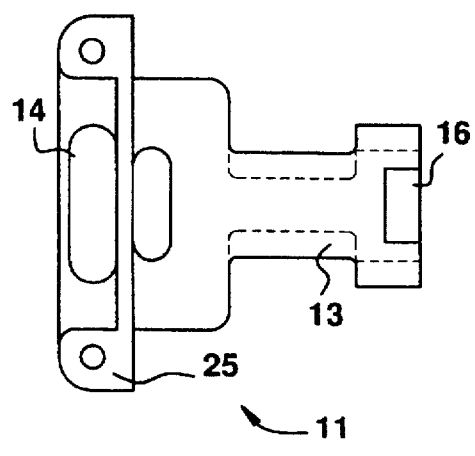
FIG. 3 is an enlarged, plan view of a spring arm component for receipt by the frame component shown in FIG. 2.
Figure 2:
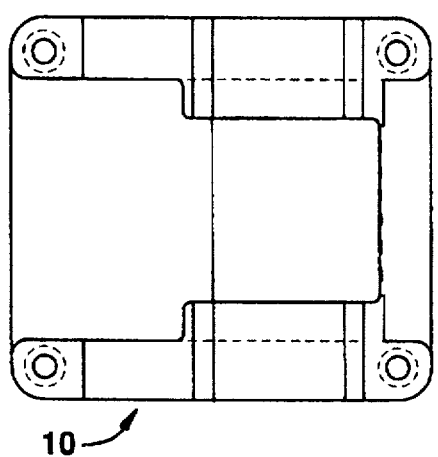
FIG. 2 is an enlarged, plan view of a frame component of a fastener casing for securing an end of the waist belt.

The fastener casing 9 includes a frame component, generally indicated 10 in FIG. 2, and a spring arm component, generally indicated 11 in FIG. 3, mounted in the frame component 10. FIGS. 2, 3, and 5 are turned 180° in relation to FIG. 1. The fastener casing 9 also includes two slides 12, as shown in FIG. 5.

The spring arm component 11 (shown in plan view in FIG. 3 and in cross-sectional side view in FIG. 4) has an elastically resilient spring arm 13. The spring arm 13 is equipped at one end with a tongue 14. The tongue 14 engages in a positive fit with a groove 15 adapted for it in the side-piece 6, as shown in FIG. 4. It will be understood that the tongue 14 can be a stud or other similar element configured for receipt in groove 15. Side-piece 6 is preferably aluminum.

The other end of the spring arm 13 is designed as a catch 16. The catch 16, when in a rest position as shown in FIG. 4, protrudes into an insertion slot 17 in frame component 10. The insertion slot 17 extends longitudinally through the fastener casing 9. In order to lock the waist belt 7 in the insertion slot 17, the end of the waist belt 7 is pushed in the direction of the arrow 18. As the end of waist belt 7 is inserted in the direction of arrow 18, the front edge of the waist belt 7 runs against a lifting bevel 19 of the catch 16. This presses the catch 16, and the spring arm 13 bearing it, upward in the direction of the arrow 28 in FIG. 4, and the spring arm 13 passes into a recess 20 in the side-piece 6.

The waist belt 7 includes a plurality of locking cutouts 21, as shown in FIG. 1. The end of the waist belt 7 is pushed into the insertion slot 17 until a locking cutout 21 defining the desired waist belt length lies under the catch 16. The catch 16 then swings, under the elastically resilient action of the spring arm 13, back into the locked position shown in FIG. 4.

To unlock the catch 16, two slides 12 are provided on either side of the frame component 10. The slides 12 can be pressed against one another manually. The slides 12 are mounted so that they can be displaced in the fastener casing 9 transverse to the insertion slot 17. The slides 12 engage the underside of the spring arm 13, which carries the catch 16, via a lifting bevel 22 formed by the inner end of each slide 12. Further pressing together of the slides 12 presses the spring arm 13 upward into its unlocked position and into the recess 20 of the side-piece 6. To facilitate its use, the outer end of each slide 12, protruding from the fastener casing 9, has a slightly inwardly curved shape to serve as an anatomically-shaped grip piece 23.

The fastener casing 9 is riveted to the side-piece 6 by rivets 24, as shown in FIG. 6. Two rivets 24 adjacent to the tongue 14 are guided through a holding piece 25 of the spring arm component 11, as shown in FIG. 5. The spring arm component 11 has an insertion bevel 26, shown in FIG. 4, that facilitates the insertion of the end of the waist belt 7 into the insertion slot 17. The insertion bevel 26 lies at the end of the spring arm component 11 into which the waist belt 7 is inserted.

To secure the locked position of the catch 16 even under loading, i.e. under the action of tensile forces exerted on it by the waist belt 7, a front end of the catch 16 has a slight bevel 27. In the event of a tensile force from the waist belt 7 applied counter to the arrow 18, the bevel 27 pulls the waist belt 7 into tight contact with the catch 16 on the spring arm 11 and thus secure the catch 16 in a locked position.

Frame component 10, spring arm component 11, and slides 12 are preferably made of plastic; the waist belt 7 is preferably made of a pliable plastic.

After reading and understanding the foregoing inventive hyperextension orthosis, in conjunction with the drawings, it will be appreciated that several distinct advantages of the subject invention are obtained. Without attempting to set forth all of the desirable features of the instant hypertension orthosis, at least some of the major advantages will be described. The overall height of the fastener casing is reduced because the material thickness of the side-piece is available for the swing arm as it swings into a recess formed in the side-piece. In regard to function, the tensile force exerted on the catch by the waist belt are absorbed by the side piece, preferably composed of metal. These forces are transferred to the side-piece via the spring arm component and its spring which engages a groove in the side-piece in a positive fit. Thus, connecting rivets or the like, which are subject to shearing forces, do not have to absorb these tensile forces.

The configuration of the subject invention also facilitates unlocking the waist belt from the fastener casing. The end of the two slides have a slightly inwardly curved surface to form an anatomically-shaped grip piece.

In order to prevent the waist belt from being withdrawn from the fastener casing due to tensile forces applied to the belt, the front edge of the catch, designed as a gently undercut bevel, absorbs the tensile forces exerted on the catch counter to the direction of insertion of the waist belt.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A hyperextension orthosis comprising:
   a base plate having at least one side-piece, said side-piece having a groove, a recess, and a free end;
   a waist belt having a plurality of locking cutouts; and
   a fastener casing mounted on said free end of said side-piece, said fastener casing formed for receiving and automatically locking an end of said waist belt, the fastener casing having
   a frame member,
   an insertion slot extending through said frame member,
   a spring arm,
   a catch formed at one end of said spring arm for operably engaging one of said plurality of locking cutouts in said waist belt under spring action when said waist belt is inserted into said insertion slot;
   opposing slides mounted to said frame member for transverse displacement relative to said insertion slot, said catch operably unlocked by displacing said opposing slides towards each other, said spring arm passing through said recess in said side-piece to unlock said catch from said one of said plurality of locking cutouts, and
   a tongue on an end of said spring arm remote from said catch, said tongue engaging said groove of said side-piece in a positive fit.

2. A hyperextension orthosis as defined in claim 1 wherein said catch protrudes outwardly from said side-piece.

3. A hyperextension orthosis as defined in claim 1 wherein said fastener casing is riveted to said side-piece.

4. A hyperextension orthosis as defined in claim 3 wherein an outer end of each of said opposing slides has an inwardly curved surface to form an anatomically-shaped grip piece.

5. A hyperextension orthosis as defined in claim 4 wherein a front edge of said catch has a beveled surface so that said front edge absorbs tensile forces exerted by said waist belt on said catch in a direction counter to a direction of insertion of said waist belt into said insertion slot.

6. A hyperextension orthosis as defined in claim 3 wherein a front edge of said catch has a beveled surface so that said front edge absorbs tensile forces exerted by said waist belt on said catch in a direction counter to a direction of insertion of said waist belt into said insertion slot.

7. A hyperextension orthosis as defined in claim 1 wherein an outer end of each of said opposing slides has an inwardly curved surface to form an anatomically-shaped grip piece.

8. A hyperextension orthosis as defined in claim 7 wherein a front edge of said catch has a beveled surface so that said front edge absorbs tensile forces exerted by said waist belt on said catch in a direction counter to a direction of insertion of said waist belt into said insertion slot.

9. A hyperextension orthosis as defined in claim 1 wherein a front edge of said catch has a beveled surface so that said front edge absorbs tensile forces exerted by said waist belt on said catch in a direction counter to a direction of insertion of said waist belt into said insertion slot.

10. A fastener casing for receiving a belt, said fastener casing comprising:

a base cover having a groove and a recess, a frame member, an insertion slot extending through said frame member, a spring arm, mounted in the frame member, a catch formed at one end of said spring arm for operably engaging one of a plurality of locking cutouts in the belt under spring action when the belt is inserted into said insertion slot, opposing slides mounted to said frame member for transverse displacement relative to said insertion slot, said catch operably unlocked by displacing said opposing slides relative to each other, said spring arm passing through said recess in said base cover to unlock said catch from an engaged one of the plurality of locking cutouts, and a tongue on an end of said spring arm remote from said catch, said tongue engaging said groove in a positive fit.

11. The fastener casing as defined in claim 10, wherein said spring arm is disposed between said base cover and said insertion slot.

* * * * *